United States Patent [19]

Klein et al.

[11] Patent Number: 4,948,389
[45] Date of Patent: Aug. 14, 1990

[54] GAS CHROMATOGRAPH HAVING CYRO BLAST COOLINGS

[75] Inventors: Kenneth J. Klein; Wei J. Song, both of Wilmington, Del.; Michael Thompson, Coatesville, Pa.

[73] Assignee: Hewlett-Packard Company, Palo Alto, Calif.

[21] Appl. No.: 355,934

[22] Filed: May 22, 1989

[51] Int. Cl.$^5$ .............................................. B01D 15/08
[52] U.S. Cl. .......................................... 55/20; 55/67; 55/197; 55/386
[58] Field of Search ................. 55/18, 20, 21, 67, 197, 55/267–269, 386, 208, 270

[56] References Cited

U.S. PATENT DOCUMENTS

| | | | |
|---|---|---|---|
| 3,174,326 | 3/1965 | Carle et al. | 55/67 X |
| 3,225,521 | 12/1965 | Burow | 55/67 |
| 3,305,000 | 2/1967 | Bullen et al. | 55/386 X |
| 3,496,702 | 2/1970 | Carel et al. | 55/67 |
| 3,527,567 | 9/1970 | Philyaw et al. | 55/67 X |
| 3,822,203 | 7/1974 | Annino et al. | 55/67 X |
| 4,035,168 | 7/1977 | Jennings | 55/197 X |
| 4,181,613 | 1/1980 | Welsh et al. | 210/179 |
| 4,269,608 | 5/1981 | Sisti et al. | 55/67 |
| 4,521,225 | 6/1985 | Jenkins et al. | 55/18 |
| 4,681,678 | 7/1987 | Leaseburge et al. | 55/386 X |
| 4,684,465 | 8/1987 | Leaseburge et al. | 55/386 X |
| 4,732,581 | 3/1988 | Cheh et al. | 55/67 |
| 4,774,190 | 9/1988 | Weiss | 55/67 X |
| 4,780,116 | 10/1988 | Cheh et al. | 55/197 X |
| 4,802,981 | 2/1989 | Kenney et al. | 55/386 X |
| 4,814,089 | 3/1989 | Kumar | 55/67 X |

Primary Examiner—Robert Spitzer
Attorney, Agent, or Firm—Richard F. Schuette

[57] ABSTRACT

Apparatus and methods are disclosed for performing a chromatographic separation of a given compound wherein the compound and a carrier gas are passed through an injection port and onto a column and wherein a portion of the column is contained in an oven. The apparatus and method are shown to include a first heater for heating the injection port in response to a first control signal, a first temperature sensor for sensing the temperature of the injection port and for generating a first temperature signal representative of the temperature of the injection port, a second heater for heating the oven in response to a second control signal, a second temperature sensor for sensing the temperature of the oven and for generating a second temperature signal representative of the temperature of the oven and a cooling member for simultaneously cooling the injection port and the column. The cooling member can include various conduit arrangements for directing a flow of cryogen fluid. There is also shown a valve for controlling the flow of cryogen fluid through the cooling member in response to a third control signal, and a control member for receiving the first and second temperature signals, and for generating the first, second and third control signals in relation to the first and second temperature signals, so that the temperature in the injection port and the oven are maintained at a desired level.

20 Claims, 3 Drawing Sheets

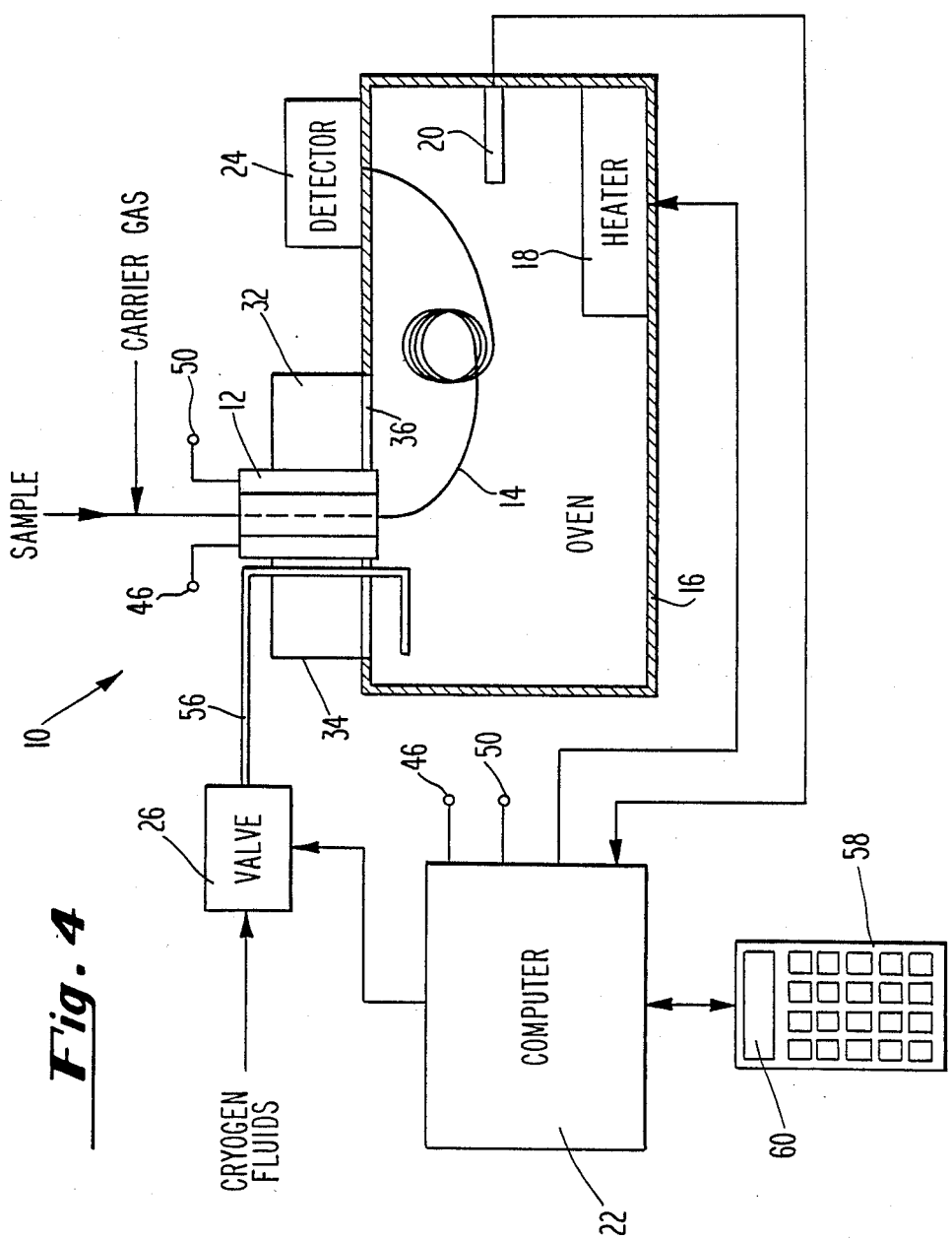

GAS CHROMATOGRAPH HAVING CYRO BLAST COOLINGS

FIELD OF THE INVENTION

The present invention relates to an advancement in the art of Gas Chromatography (GC) and, more particularly, to a GC system capable of temperature regulation below room temperature.

BACKGROUND OF THE INVENTION

In analytical chemistry, liquid and gas chromatography techniques have become important tools in the identification of chemical sample components. The basic principle underlying all chromatographic techniques is the separation of a sample chemical mixture into individual components by transporting the mixture in a moving fluid through a porous retentive media. The moving fluid is referred to as the mobile phase and the retentive media has been referred to as the stationary phase. One of the differences between liquid and gas chromatography is that the mobile phase is either a liquid or a gas, respectively.

In a gas chromatograph, typically, a supply of inert carrier gas (mobile phase) is continually passed as a stream through a heated column containing porous sorptive media (stationary phase). GC columns have also been known to comprise a hollow capillary tube having an inner diameter in the range of few hundred microns. A sample of the subject mixture is injected into the mobile phase stream and passed through the column. As the subject mixture passes through the column it separates into its various components. Separation is due primarily to differences in the volatility characteristics of each sample component with respect to the temperature in the column. A detector, positioned at the outlet end of the column, detects each of the separated components as they exit the column.

The analytical choice between liquid and gas chromatography techniques is largely dependent on the molecular weight of the compound being analyzed. Liquid chromatographs are capable of analyzing much heavier compounds than gas chromatographs. However, since gas chromatography detection techniques are more sensitive, they are preferred.

The advent of Supercritical Fluid Chromatography (SFC) provided a potential bridge between gas and liquid chromatography advantages, i.e., high sensitivity and heavier molecular weight samples. In SFC, a fluid heated above the critical point, is used as the mobile phase. Such fluid is passed under pressure through a media which differentially retains sample components. As the pressure of the mobile phase is increased, for example, from about 40 ATM to approximately 400 ATM, the sample being analyzed separates into its various components dependent upon the relative differential solubility of each component with the mobile phase. Since the mobile phase is a gas, detectors used in GC can be utilized, significantly enhancing detection sensitivity and selectivity.

SFC has been found to be primarily useful in the analysis of moderate molecular weight homologous series (M.W. 100 to 10,000) and some thermally labile molecules such as pesticides and pharmaceuticals. The problem with SFC, however, is the long period of time involved in conducting a sample analysis. Although GC techniques are faster than SFC techniques, extended periods of time can occur between GC analyses, which is also undesirable. Time between GC analyses is generally related to cooling of the inlet or oven used in a first test to a suitable temperature prior to starting a second test.

It has been known in the past to program temperature in gas chromatographic analyzation since separation of the sample components is due primarily to differences in the volatility characteristics of each component with respect to the temperature in the column. By raising the column temperature either in a constant linear fashion or in a variable non-linear fashion over a sufficient range of temperature one can assure high resolution detection of all sample components in a minimized time period. High resolution is assured because each component is emerging from the column at its optimum temperature. Since the highest temperatures occur at the end of a test, it is necessary to cool the chromatographic apparatus before beginning the next analysis.

As used herein the term resolution refers to the distinctness of graphed peaks generated by known detection apparatus, wherein each peak is representative of the detection of a sample component.

It has also been known in the past that the time required between temperature programmed GC analyses can be reduced by providing a coolant in various sections of the chromatographic equipment, such as the oven or the injection apparatus to bring the temperature in that section down to a desired level prior to beginning the next analysis. In addition it has been known during a GC analysis to utilize a temperature profile which has a portion below room temperature, particularly in the analysis of highly volatile components. Along these lines, various devices are known for cooling the oven or cooling the injection apparatus.

U.S. Pat. No. 4,269,608 — Sisti et al. discloses an injector for providing a sample gas in a so-called "on column" injection technique. In on column injection, the sample gas is injected directly into the inlet end of the column and is not first passed through a splitter type device. In Sisti the injector apparatus is shown, in one embodiment, to have a coil which is said to be capable of drawing heat from the injector by passing a fluid at a suitable temperature therethrough.

The problem with these prior devices and techniques is that cooling and heating of the oven and injection apparatus is achieved independently of one another. During cool down between analyses, cooling of the oven can become a bottleneck because a greater amount of heat needs to be removed. Additionally, redundant hardware is required and non-optimal use of the cooling fluid can occur. Consequently, a need still exists for a GC apparatus which optimize coolant use, minimizes required hardware and which minimizes the time between analyses necessary for cool down.

SUMMARY OF THE INVENTION

The advantages of the invention are achieved in a method and apparatus for performing a chromatographic separation of a given compound wherein the compound and a carrier gas are passed through an injection port and onto a column and wherein a portion of the column is contained in an oven. The apparatus and method are shown to include a first heater for heating the injection port in response to a first control signal, a first temperature sensor for sensing the temperature of the injection port and for generating a first temperature signal representative of the temperature of the injection port, a second heater for heating the oven in response to a second control signal, a second temperature sensor for sensing the temperature of the oven and for generating a second temperature signal representative of the temperature of said oven and a cooling member for simultaneously cooling the injection port and the column. The cooling member can include various conduit arrangements for directing a flow of cryogen fluid. There is also shown a valve for controlling the flow of cryogen fluid through the cooling member in response to a third control signal, and a control member for receiving the first and second temperature signals, and for generating the first, second and third control signals in relation to the first and second temperature signals, so that the temperature in the injection port and the oven are maintained at a desired level.

BRIEF DESCRIPTION OF THE DRAWINGS

The present invention will be better understood, and its numerous objects and advantages will become apparent by reference to the following detailed description of the invention when taken in conjunction with the following drawings, in which:

FIG. 4 is a block diagram of a still further embodiment of a gas chromatograph constructed in accordance with the present invention.

DETAILED DESCRIPTION OF THE PREFERRED EMBODIMENT

Figure 1:
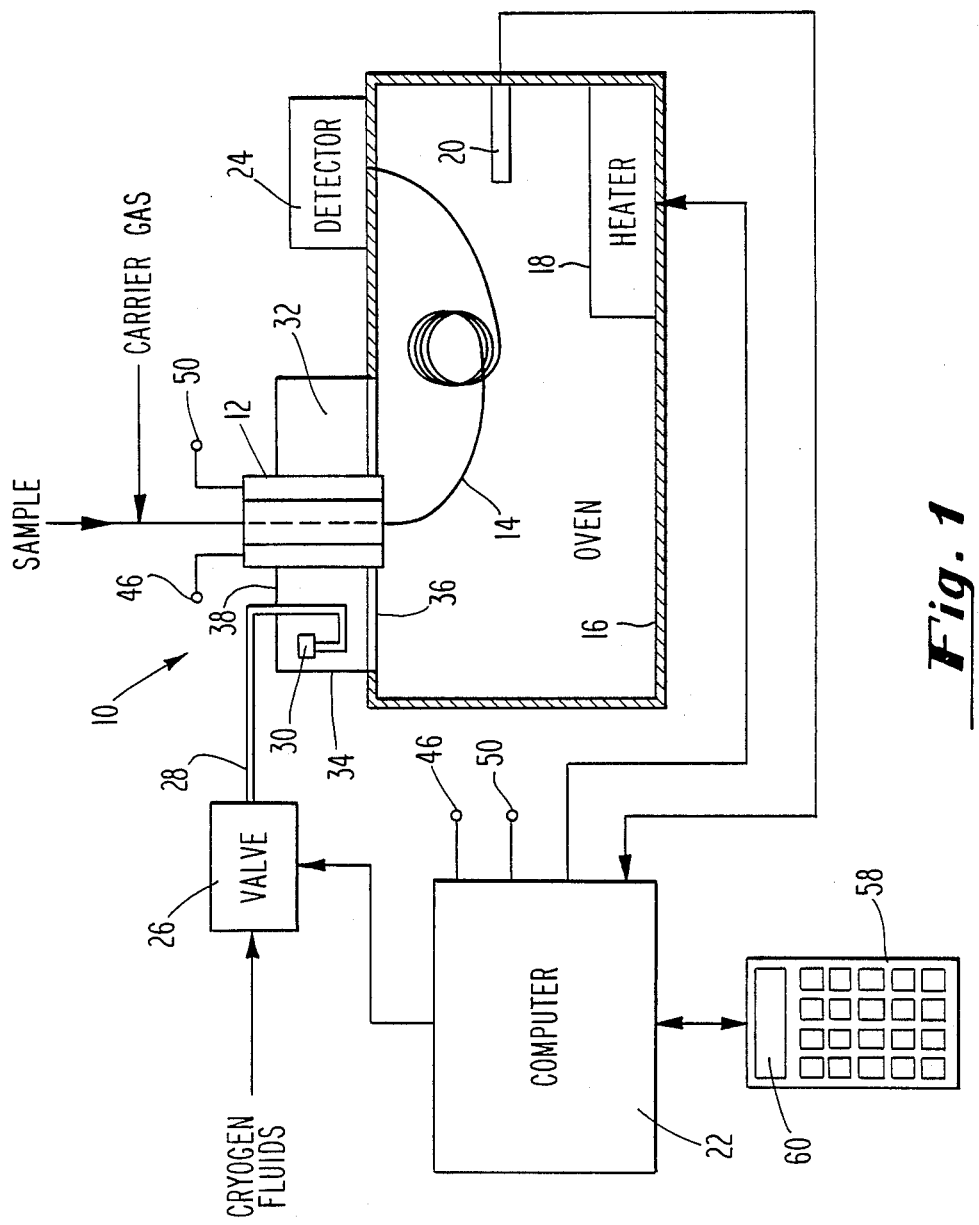
FIG. 1 is a block diagram of a forward pressure regulated gas chromatograph constructed in accordance with the present invention.

A new and novel gas chromatograph is shown in FIG. 1 and is generally designated 10. Although not shown in FIG. 1, chromatograph 10 is arranged in a forward pressure regulated design suitable for direct, i.e. non-split, injections. In order to perform a chromatographic separation of a given sample compound, the sample is injected using a so-called "on column" technique with a pressurized carrier gas by means of an injection port 12. The carrier gas supplied to injection port 12 is provided from a source through an appropriate valve (not shown), which serves to control the pressure of the carrier gas in the GC system.

Column 14 is positioned within oven 16. Although no particular oven design is necessary in order to comply with the principles of the present invention, the oven should include a heating unit 18 and a temperature sensor 20. Heating unit 18 provides heat to oven 16 in response to a control signal generated by computer 22 which will be described in greater detail herein. In order to ensure that the temperature within the oven is at a desired level, sensor 20 generates a feedback signal representative of the temperature in oven 16, which signal is provided to computer 22. The carrier gas/sample combination passing through column 14 is exposed to a temperature profile resulting in part from the operation of heater 18 within oven 16. Typically, the temperature in oven 16 is increased from a minimum level to a maximum level in a linear and non-linear fashion. During this profile of changing temperatures, i.e., rising or falling, the sample will separate into its components primarily due to differences in the volatility characteristics of each component at a given temperature. As the components exit column 14 they are detected by detector 24. Detector 24 can be any of the known GC detectors such as a flame ionization detector or a mass spectrometer.

A portion of the temperature profile envisioned to be applied to column 14 in oven 16 will be below ambient or room temperature. The desired temperatures in this portion of the temperature profile are achieved through the use of a cryogen fluid which is dispersed within oven 16. Cryogen fluid of any appropriate type, such as liquid carbon dioxide, liquid nitrogen, or compressed air, is provided from a source not shown to valve 26. Valve 26 is open and closed in relation to the receipt of a control signal from computer 22. When valve 26 is open, the cryogen fluid is passed through tube 28 and restrictor 30 into chromatograph 10. As shown in FIG. 1, the cryogen fluid is deposited into an inlet chamber 32, which chamber is defined by inlet cover 34. Inlet cover 34 surrounds opening 36 in oven 16 so that fluid communication is established therebetween. As will be appreciated, cryogen fluid exiting restrictor 30 will pass into chamber 32, through opening 36 and into oven 16. As shown in FIG. 1, restrictor 30 is directed so that cryogen fluid exiting restrictor 30 is directed upwards towards the top wall 38 of cover 34. Cryogen fluid passing through opening 36 serves to cool the interior of oven 16. Computer 22 controls the time during which valve 26 remains open in relation to the temperature sensed in oven 16 by sensor 20.

Figure 2:
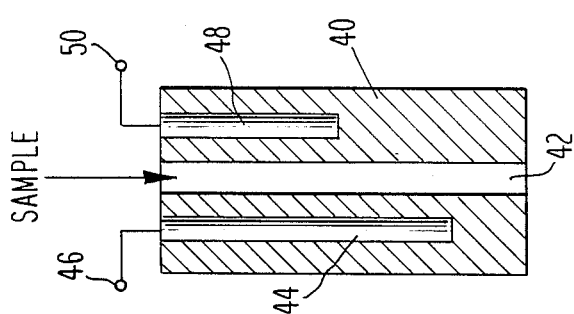
FIG. 2 is a cross-sectional view of the injection part shown in FIG. 1.

Injection port 12 is shown in greater detail in FIG. 2, wherein injection port 12 is shown to include a block 40 into which a series of bores have been formed. Block 40 is constructed of a thermally conducted material, such as aluminum. The sample/carrier gas combination is passed through central bore 42 and onto column 14. A cartridge heater 44 is provided for heating block 40 in response to an actuation signal being provided at terminal 46. The temperature of block 40 is sensed by sensor 48 which generates an electrical signal representative of the temperature of block 40, which signal in turn is output in terminal 50. Heater 44 in turn raises the temperature of block 40 to a desired level whereupon computer 22, based upon the signal from sensor 48, modifies the control signal supplied to terminal 46. It will also be noted that sensor 48 can be used by computer 22 in generating the control signal for valve 26.

As cryogen fluid is dispersed within chamber 32, the temperature of block 40 will also be modified. Any modifications to the temperature of block 40 will be sensed by sensor 48 and thus transmitted to computer 22 at terminal 50.

Figure 3:
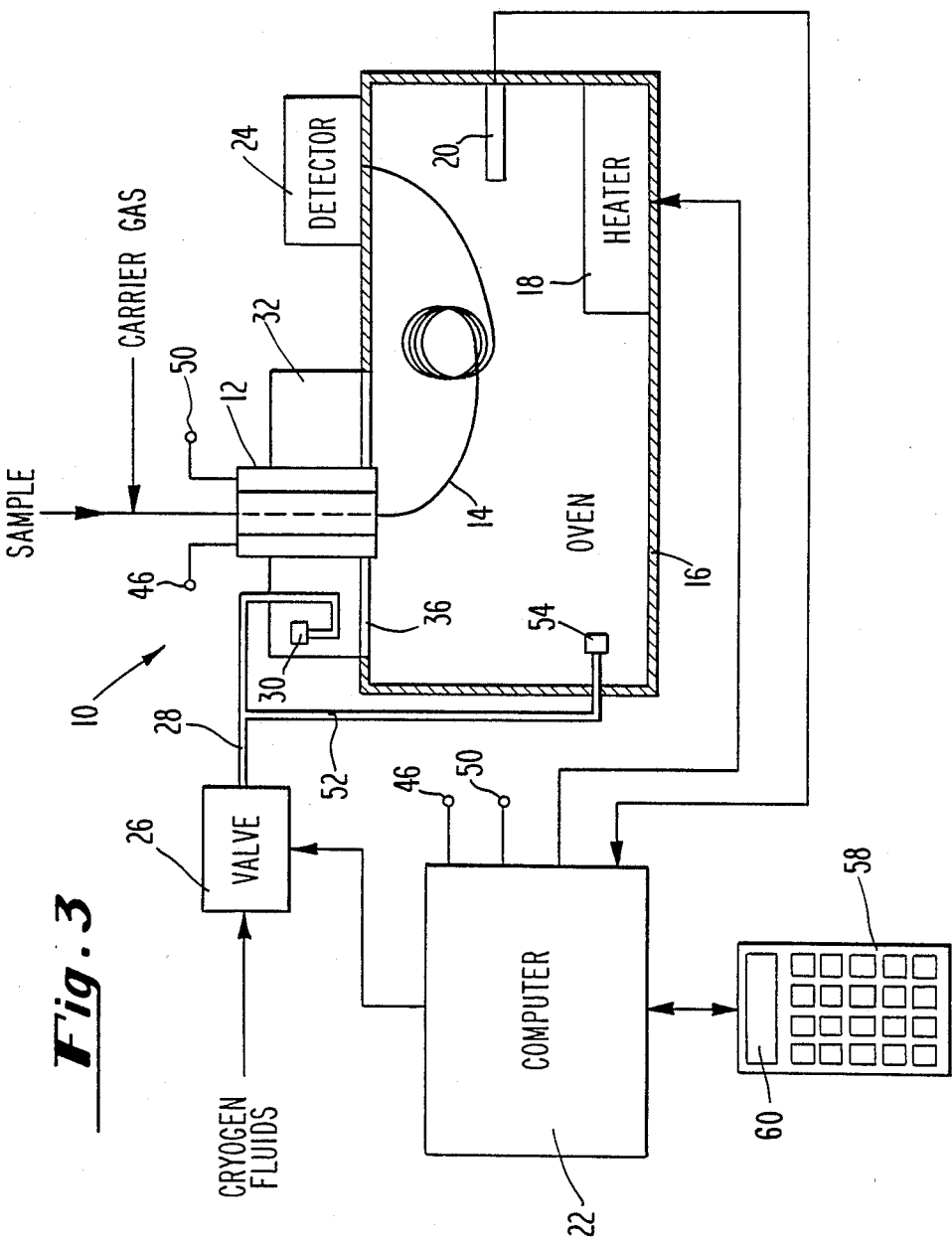
FIG. 3 is a block diagram of another embodiment of a gas chromatograph constructed in accordance with the present invention.

As shown in FIG. 3, chromatograph 10 includes basically identical components as was described in relation to FIG. 1. In FIG. 3, however, tube 28 is provided with a branch tube 52 which extends into oven 16 and has restrictor 54 attached by any suitable means to the end thereof. As will be appreciated upon review of FIG. 3, cryogen fluid is provided simultaneously through restrictor 30 into chamber 32 and through restrictor 54 into oven 16. It will be noted that a single valve 26 is utilized to control the supply of cryogen fluid to restrictors 30 and 54. In the preferred embodiment, the amount of cryogen fluid provided to oven 16 will be greater than that provided to chamber 32. The ratio between the orifice diameters of restrictors 30 and 54, preferably 10:1 or greater, will determine the ratio between cryogen fluid provided to chamber 32 and oven 16. In the preferred embodiment, the orifice diameter of restrictor 54 is approximately 0.38 mm and restrictor 30 is a 5000-¼×¼-100 restrictor manufactured and sold by Mott Metallurgical Corporation of Farmington, CN.

Referring now to FIG. 4, there is shown still another embodiment of chromatograph 10. As shown in FIG. 4, tube 28 has been replaced by tube 56. Tube 56 is constructed by a thermally conductive material, such as aluminum. Tube 56 is shown to extend a distance along the length of and proximate to injection port 12 through opening 36 and into oven 16. The open end of tube 56 is directed towards a sidewall of oven 16. The passage of cryogen fluid through tube 56 serves both to cool injection port 12 and oven 16. The cooling of injection port 12 results from convection cooling which occurs between injection port 12 and thermally conductive tube 56. Oven 16 is cooled by the dispersement of the cryogen fluid therein. It will be noted that when liquid nitrogen is utilized as the cryogen fluid, it is preferred that tube 56 have an inner diameter of approximately one quarter inch. The size and length of tube 56 gives the proper restriction to control the flow rate of the liquid nitrogen.

In the preferred embodiment, oven 16 is a Hewlett-Packard 5890A gas chromatograph. Such a gas chromatograph includes an internal fan, (not shown) which is more fully described in U.S. Pat. No. 4,181,613 Welsh, et al. which is incorporated herein by reference. The action of the fan in oven 16 will serve to drive a small portion of the liquid nitrogen through opening 36 and into chamber 32. This small portion will also serve to cool injection port 12.

Referring to FIG. 1, the electronic controls are shown to include two main components, namely keypad 58, and computer 22. Computer 22 maintains overall control of all systems associated with gas chromatograph 10. It will be recognized that any particular gas chromatograph may include more systems than those described in relation to the present invention. It will also be understood that although computer 22 is shown as a single block, such computer includes a central processing unit and all associated peripheral devices, such as random access memories, read-only memories, input/output isolation devices, clocks and other related electronic components. In the preferred embodiment, the central processor used in computer 22 is a Z80 microprocessor. As such, computer 22 includes a memory in which information and programming can be stored and retrieved by known methods. The programming associated with computer 22 which is utilized in relation to the present invention will be readily understood from the description herein.

Two of the functions of computer 22 is the control of oven temperature and injection port temperature. Computer 22 controls oven temperature by transmitting an appropriate signal to heater 18 which causes heater 18 to increase or decrease the amount of heat transferred to oven 16 and/or by transmitting an appropriate signal to valve 26 which initiates or terminates the disbursement of cryogen fluid within oven 16. Sensor 20 senses the temperature in oven 16 and transmits a feedback signal representative of such temperature to computer 22. By monitoring the temperature feedback signal from sensor 20 computer 22 can maintain the temperature in oven 16 at some desired level by controlling heater 18 and valve 26. Operating commands and other information are entered into computer 22 by way of keypad 58. The particular information entered through keypad 58 which relates to the present invention is described herein. Keypad 58 in the preferred embodiment is provided with a display screen 60. Consequently, indicating or prompt messages can be generated by computer 22 and displayed on keypad 58.

Computer 22 controls temperature of injection port 12 by transmitting an appropriate signal to heater 44 which causes heater 44 to increase or decrease the amount of heat transferred to block 40 and/or by transmitting an appropriate signal to valve 26 which will initiate or terminate the disbursement of cryogen fluids within chamber 32. Sensor 48 senses the temperature of block 40 and transmits a feedback signal representative of such block temperature to computer 22. By monitoring the temperature feedback signal from sensor 48, computer 22 can maintain the temperature of block 40 at some desired level through the control of either heater 48 or valve 26. Although FIGS. 1, 3 and 4 disclose different cryogen fluid disbursement systems, computer 22 maintains the temperature of injection port 12 or oven 16 in the same manner.

Computer 22 in the preferred embodiment generates a control signal which is used to control valve 26, heater 18 and heater 44. Since the generated control signal will be in a digital form it is converted to analog form by a digital to analog converter (not shown) and appropriately amplified.

Consider now that portion of the operation of computer 22 which relates to and is in accordance with the present invention. There will now be described those procedures necessary to program or set the GC system so that a particular gas chromatographic separation test or run can be conducted. Several pieces of information are entered into computer 22 by the user through way of keypad 58. With one processing exception which will be described, computer 22 operates to store the entered information into memory for later access.

Initially parameters relating to the temperature profile to be provided by oven 16 and injection port 12 during the analysis are entered through keyboard 58. In the preferred embodiment, desired temperatures for any given moment in time during the analysis is calculated by computer 22 in relation to such temperature profile parameters. In the preferred embodiment, such oven temperature calculations are performed at a rate of 40 Hz. Basically, each item of temperature information represents the desired temperature of oven 16 or injection port 12 at a particular point in time during a chromatographic analysis. Accordingly, it will be necessary to enter an initial temperature and an initial time, a final temperature and a final time and the rate at which it is desired for the oven or injection port temperature to proceed from the initial temperature to the final temperature for the time period existing between the initial time and the final time. Having entered this information, it is a relatively simple operation for computer 22 to generate a desired temperature in real time. To regulate the temperature of oven 16 or injection port 12, the calculated desired temperature is used as a control signal.

Since the desired temperature of oven 16 or injection port 12 has been calculated, and since the actual temperature of oven 16 is known from sensor 20 and the actual temperature of block 40 is known from sensor 48, it is a relatively simple operation for computer 22 to regulate the temperature of the injection port or the oven.

While the invention has been described and illustrated with reference to specific embodiments, those skilled in the art will recognize that modification and variations may be made without departing from the principles of the invention as described herein above and set forth in the following claims.

What is claimed is:

1. A method for performing a chromatographic separation of a given compound wherein said compound and a carrier gas are passed through an injection port and onto a column and wherein a portion of said column is contained in an oven, comprising the steps of:
   heating said injection port in response to a first control signal;
   sensing the temperature of said injection port and for generating a first temperature signal representative of the temperature of said injection port;
   heating said oven in response to a second control signal;
   sensing the temperature of said oven and for generating a second temperature signal representative of the temperature of said oven;
   simultaneously cooling said injection port and said column, by directing a flow of cryogen fluid through a volume, said volume located proximate said injection port and said column;
   providing a valve for controlling the flow of cryogen fluid in response to a third control signal; and
   controlling the temperature during said chromatographic separation by receiving said first and second temperature signal, and generating said first, second and third control signals in relation to said first and second temperature signals, so that the temperature in said injection port and said oven are maintained at a desired level.

2. The method of claim 1, further comprising the step of providing an inlet cover surrounding said injection port and defining a portion of said volume, positioning said injection port in an opening formed in said oven and wherein said inlet cover surrounds said opening.

3. The method of claim 2, wherein said step of simultaneously cooling comprises the step of, extending a conduit through said cover, said conduit having one end connected to said valve and a restrictor connected to the other end of said conduit, and disbursing cryogen fluid in said volume so that said cryogen fluid will cool said injection port and will flow through said opening in said oven into said oven.

4. The method of claim 3, wherein said inlet cover has a top wall and further comprising the step of orienting said restrictor so that cryogen fluid exiting said restrictor will be directed toward said top wall.

5. The method of claim 4, further comprising the step of providing a second conduit having one end connected to said conduit so that said valve controls the flow of cryogen fluid through said conduit and said second conduit, extending said second conduit into said oven and providing a second restrictor attached to said second conduit.

6. The method of claim 5, further comprising the step of sizing the orifice diameter of said first and second restrictors so that the ratio of said orifice diameters equals a predetermined value.

7. The method of claim 6, wherein the ratio of said orifice diameter of said second restrictor to said orifice diameter of said restrictor is approximately 10:1.

8. The method of claim 2, wherein said step of cooling comprises the steps of, providing a thermally conductive conduit, extending said conduit through said cover, through said volume, through said opening and into said oven, so that cryogen fluid allowed to pass through said conduit by said valve will be disbursed in said oven and said injection port will be cooled by convection cooling between said conduit and said injection port.

9. The method of claim 8, further comprising the step of positioning a portion of said conduit proximate said injection port in said volume.

10. The method of claim 9, wherein said oven has side walls and further comprising the step of orienting the open end of said conduit so that cryogen fluid is directed against one of said side walls.

11. An apparatus for performing a chromatographic separation of a given compound wherein said compound and a carrier gas are passed through an injection port and onto a column and wherein a portion of said column is contained in an oven, comprising:
    first heating means for heating said injection port in response to a first control signal;
    first temperature sensor means for sensing the temperature of said injection port and for generating a first temperature signal representative of the temperature of said injection port;
    second heating means for heating said oven in response to a second control signal;
    second temperature sensor means for sensing the temperature of said oven and for generating a second temperature signal representative of the temperature of said oven;
    cooling means for simultaneously cooling said injection port and said column, said cooling means comprising means for directing a flow of cryogen fluid;
    a valve for controlling the flow of cryogen fluid through said cooling means in response to a third control signal; and
    control means for receiving said first and second temperature signal, and for generating said first, second and third control signals in relation to said first and second temperature signals, so that the temperature in said injection port and said oven are maintained at a desired level.

12. The apparatus of claim 11, further comprising an inlet cover surrounding said injection port and defining a volume, wherein said injection port is positioned in an opening formed in said oven and wherein said inlet cover surrounds said opening.

13. The apparatus of claim 12, wherein said cooling means comprises, a conduit extending through said cover, said conduit having one end connected to said valve and a restrictor connected to the other end of said conduit, so that cryogen fluid allowed to pass through said conduit by said valve will be disbursed in said volume and will flow through said opening in said oven into said oven.

14. The apparatus of claim 13, wherein said inlet cover has a top wall and wherein said restrictor is oriented so that cryogen fluid exiting said restrictor will be directed toward said top wall.

15. The apparatus of claim 14, further comprising a second conduit having one end connected to said conduit so that said valve controls the flow of cryogen fluid through said conduit and said second conduit, said second conduit extending into said oven and having a second restrictor attached thereto.

16. The apparatus of claim 15, wherein said restrictor and said second restrictors have orifice diameters sized so that the ratio of said orifice diameters equals a predetermined value.

17. The apparatus of claim 16, wherein the ratio of said orifice diameter of said second restrictor to said orifice diameter of said restrictor is approximately 10:1.

18. The apparatus of claim 12, wherein said cooling means comprises, a thermally conductive conduit extending through said cover, through said volume, through said opening and into said oven, so that cryogen fluid allowed to pass through said conduit by said valve will be disbursed in said oven and said injection port will be cooled by convection cooling between said conduit and said injection port.

19. The apparatus of claim 18, wherein a portion of said conduit is positioned proximate said injection port in said volume.

20. The apparatus of claim 19, wherein said oven has side walls and wherein the open end of said conduit is oriented to direct cryogen fluid against one of said side walls.

* * * * *